United States Patent
Rhodes et al.

(10) Patent No.: US 12,128,201 B2
(45) Date of Patent: Oct. 29, 2024

(54) CAPSULE DEVICE FOR DELIVERY OF ACTIVE AGENT TO GASTROINTESTINAL TRACT

(71) Applicant: BAYWIND BIOVENTURES, San Diego, CA (US)

(72) Inventors: Christopher A. Rhodes, San Diego, CA (US); Jose Casillas, Chula Vista, CA (US)

(73) Assignee: Baywind Bioventures, San Diego, CA (US)

( * ) Notice: Subject to any disclaimer, the term of this patent is extended or adjusted under 35 U.S.C. 154(b) by 692 days.

(21) Appl. No.: 17/270,424

(22) PCT Filed: Aug. 23, 2019

(86) PCT No.: PCT/US2019/048034
§ 371 (c)(1),
(2) Date: Feb. 22, 2021

(87) PCT Pub. No.: WO2020/041774
PCT Pub. Date: Feb. 27, 2020

(65) Prior Publication Data
US 2021/0213263 A1    Jul. 15, 2021

Related U.S. Application Data

(60) Provisional application No. 62/722,083, filed on Aug. 23, 2018.

(51) Int. Cl.
*A61M 31/00* (2006.01)
*A61K 9/00* (2006.01)
(Continued)

(52) U.S. Cl.
CPC ......... *A61M 31/002* (2013.01); *A61K 9/0007* (2013.01); *A61K 9/0065* (2013.01);
(Continued)

(58) Field of Classification Search
CPC .. A61M 31/002; A61K 9/0065; A61K 9/0053
See application file for complete search history.

(56) References Cited

U.S. PATENT DOCUMENTS

| 2004/0253304 A1 | 12/2004 | Gross et al. |
| 2007/0225633 A1 | 9/2007 | Ferren et al. |

(Continued)

FOREIGN PATENT DOCUMENTS

| WO | WO-2004/002565 A1 | 1/2004 |
| WO | WO-2011/079302 A2 | 6/2011 |

*Primary Examiner* — Tiffany Legette
*Assistant Examiner* — Macy C Frank
(74) *Attorney, Agent, or Firm* — Mintz, Levin, Cohn, Ferris, Glovsky and Popeo, P.C.

(57) ABSTRACT

An oral delivery capsule device for delivering an active agent to a part of a gastrointestinal (GI) tract of a subject may include a capsule body configured to travel along the GI tract. The capsule device may include a reservoir configured to contain an active agent for delivery to the GI tract of the subject. The oral delivery capsule device may include an actuation feature configured to provide a delivery force thereby causing the dispensing of the active agent. The oral delivery capsule device may include an actuation control feature configured to prevent actuation of the actuation feature under a first condition and allow actuation under a second condition.

33 Claims, 6 Drawing Sheets

(51) Int. Cl.
  *A61K 9/46* (2006.01)
  *A61K 9/48* (2006.01)
(52) U.S. Cl.
  CPC .......... *A61K 9/0097* (2013.01); *A61K 9/4808* (2013.01); *A61K 9/4891* (2013.01); *A61M 2205/0238* (2013.01); *A61M 2205/3324* (2013.01); *A61M 2210/1042* (2013.01)

(56) References Cited

U.S. PATENT DOCUMENTS

| | | | |
|---|---|---|---|
| 2007/0281007 A1* | 12/2007 | Jacob | A61K 31/74 |
| | | | 514/471 |
| 2008/0194912 A1 | 8/2008 | Trovato et al. | |
| 2011/0160699 A1* | 6/2011 | Imran | A61M 5/1723 |
| | | | 604/93.01 |
| 2017/0246438 A1 | 8/2017 | Aran et al. | |
| 2018/0169003 A1 | 6/2018 | Imran | |
| 2018/0368730 A1 | 12/2018 | Moshiree | |

\* cited by examiner

CAPSULE DEVICE FOR DELIVERY OF ACTIVE AGENT TO GASTROINTESTINAL TRACT

CROSS-REFERENCE TO RELATED APPLICATION

This application is a national stage application, filed under 35 U.S.C. § 371, of International Patent Application No. PCT/US19/48034, filed Aug. 23, 2019, entitled "CAPSULE DEVICE FOR DELIVERY OF ACTIVE AGENT TO GASTROINTESTINAL TRACT", which claims priority to U.S. Provisional Patent Application No. 62/722,083, filed on Aug. 23, 2018, entitled "CAPSULE DEVICE FOR ORAL DELIVERY OF BIOLOGICS", the disclosure of which is incorporated herein by reference in its entirety.

TECHNICAL FIELD

The subject matter described herein relates to an oral delivery device for delivering an active agent to a part of a gastrointestinal tract of a subject.

BACKGROUND

Most conventional formulation approaches for delivering biologics (e.g., permeation enhancers and tight junction openers) can result in very low bioavailability of active agent into the blood of the subject. For example, oral delivery of salmon calcitonin (a 34 amino acid peptide) in a tablet formulation containing lauryl carnitine, citric acid, and standard tablet excipients may only be able to achieve approximately 1 to 2% bioavailability from the tablet into the blood stream.

Some devices have been developed to address the biologics oral delivery problems outlined above. In this device, a drug is encapsulated into microneedles, which are designed to be triggered to release the drug in the gastrointestinal (GI) tract, and push the drugs into walls of the GI tract using a propulsive force. This device has been documented to achieve over 30% bioavailability for biologics of all sizes, as the microneedles are able to penetrate the highly vascularized tissue of the GI tract, delivering the drugs, which are rapidly dissolved off of the microneedles, rapidly into the bloodstream. This microneedle device was the first system to attempt to demonstrate the benefit of delivering agents directly into the wall of the GI tract to achieve a high bioavailability.

However, one of the limitations of the microneedle device system is drug loading. Microneedles can only achieve delivery of 1 to 3 mg due to the low surface area on the microneedles. Even for solid microneedle systems, the drug load is less than 5 to 10 mg for a large surface-area microneedle patch. Further complicating the matter of size in the GI tract is the shear limitation of a capsule that can be swallowed by a subject. The largest common capsule size is a "000 capsule," and is quite large for most patients. The size is approximately 25 mm in length by 10 mm in width. These physical dimensions limit the microneedle to have to fit into the inner diameter of the capsule, along with the other device-related mechanisms that are built into the capsule, thereby limiting the dose in a capsule (e.g., less than 3 mg). In addition, manufacture of microneedles is complicated and inefficient such that large scale manufacturing is highly specialized and costly, requiring new manufacturing processes that are not standard in the pharmaceutical industry.

Hence, there is a need for a device and system for delivery of agents into and onto the tissue of the GI tract which overcome the issues outlined above, such as bioavailability, manufacturability, cost of goods for each capsule, and mass of agent that can be delivered in a single administration.

SUMMARY

Aspects of the current subject matter include various embodiments of a delivery capsule device that can be swallowed by a patient or inserted into a gastrointestinal (GI) tract of the patient. The capsule device can contain at least one active agent that can be delivered to a part of the GI tract.

Aspects of the current subject matter relate to methods and system for an oral delivery capsule device for delivering an active agent to a part of a gastrointestinal (GI) tract of a subject. In one aspect, a method for an oral delivery capsule device is described.

In some variations, one or more of the following features may optionally be included in any feasible combination. The oral delivery capsule device may include a capsule body configured to travel along the GI tract. The capsule body may have a capsule wall defining an inner body portion. The oral delivery capsule device may include a reservoir positioned in the inner body portion and configured to contain an active agent for delivery to the part of the GI tract of the subject. The oral delivery capsule device may include an actuation feature configured to provide a delivery force to the active agent thereby causing the dispensing of the active agent from the capsule body through a delivery port along the capsule wall. The oral delivery capsule device may include an actuation control feature configured to prevent actuation of the actuation feature under a first condition and allow actuation of the actuation feature under a second condition.

In some variations one or more of the following features can optionally be included in any feasible combination. The actuation feature may include a spring configured to transition between a first position and a second position thereby causing the dispensing of the active agent through the delivery port. The oral delivery capsule device may include a plunger configured to advance towards the delivery port when the spring transitions between the first position and the second position. The oral delivery capsule device may include a coating positioned over at least the delivery port and may be configured to prevent fluid passage through the delivery port when the coating is exposed to a first pH range and may allow fluid passage through the delivery port when the coating is exposed to a second pH range. The second condition may include contact of GI fluid with the actuation control feature.

In some embodiments, the capsule wall of the capsule body may include an intake port configured to allow GI fluid to enter the inner body portion and contact the actuation control feature. The actuation control feature may include an enteric coated tablet configured to dissolve when under the second condition. The second condition may include exposure to a fluid having a pH within a predefined pH rage. The actuation control feature may include a polymer coated tablet configured to dissolve when under the second condition. The second condition may include the passage of a pre-defined time. The actuation feature may include a biodegradable plastic that dissolves when under the second condition. The second condition may include contact with GI fluids.

In some embodiments, an outer surface of the capsule wall may include a coating including a muco-adhesive material that may assist with mating of the capsule body to a part of the GI tract. The outer surface of the capsule wall may include a surface feature that may assist with mating the capsule body to a part of the GI tract.

In some embodiments, the actuation control feature may include a propulsion formulation that may create a propulsion force after being placed in contact with GI fluid. The delivery port may be configured to releasably couple a nozzle therein. The nozzle may affect a characteristic of fluid delivery from the delivery port. The oral delivery capsule device may include a plurality of delivery ports positioned radially along a first end of the capsule body. The active agent may include one or more of a peptide, a protein, an antibody, an oligonucleotide, a polysaccharide, a small molecule organic drug, an inorganic drug, a therapeutic agent, a diagnostic agent, and a tissue coating agent. The capsule body may be made out of a biocompatible and biodegradable material.

In another interrelated aspect of the current subject matter, a method includes receiving a GI fluid through an intake port of a capsule wall of a capsule delivery device. The capsule delivery device may include a capsule body configured to travel along the GI tract. The capsule body may include the capsule wall defining an inner body portion. The method may include a reservoir positioned in the inner body portion and configured to contain an active agent for delivery to the part of the GI tract of the subject. The method may include an actuation feature configured to provide a delivery force to the active agent thereby causing the dispensing of the active agent from the capsule body through a delivery port along the capsule wall. The method may include an actuation control feature configured to prevent actuation of the actuation feature under a first condition and allow actuation of the actuation feature under a second condition. The method may include actuating, as a result of the received fluid contacting the actuation control feature. The actuation feature may thereby provide the delivery force to the active agent. The method may include delivering the active agent through the delivery port of the capsule wall.

In some embodiments, the method may include dissolving the actuation control feature as a result of the received GI fluid contacting the actuation control feature. The actuating feature may include a spring. The actuating may include allowing the spring to transition from a compressed configuration to an expanded configuration. Actuating the actuation feature may cause a plunger to be advanced along the reservoir thereby causing the delivering of the active agent.

In some embodiments, the actuation control feature may include a propulsion formulation that creates a propulsion force after being placed in contact with GI fluid. The actuating of the actuation control feature may create a propulsion force through a vent extending through the capsule wall thereby propelling the capsule device toward a surface of the GI tract.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1B:
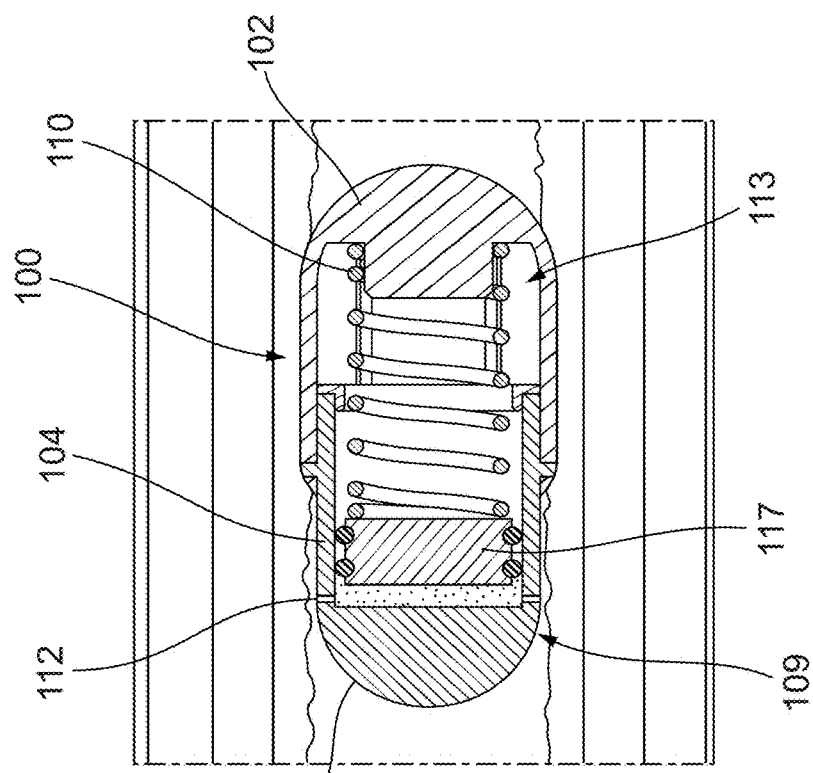
FIG. 1B illustrates the capsule delivery device of FIG. 1A showing the active agent dispensed from the capsule delivery device.

This disclosure describes various embodiments of a capsule delivery device that can be orally delivered (e.g. swallowed) for allowing the capsule delivery device to travel along the gastrointestinal (GI) tract of a subject to deliver one or more active agents along a part of the GI tract.

In some embodiments, at least some of the capsule delivery device is made out biocompatible material and configured to deliver active agents to various surfaces and tissues of the gastrointestinal (GI) tract. For example, the capsule delivery device can be designed to spray a formulation composition including at least one active agent onto and into an inside surface of the GI tract, such as by using a propulsive force generated inside the capsule delivery device (e.g., by a spring).

In some embodiments, the capsule delivery device may be designed to release its contents in varying locations of the GI tract, such as depending on a triggering mechanism used (e.g., enteric coated polymers, or other water and pH sensitive materials). The capsule delivery device can be made of inert and/or bio-safe materials that are well known in pharmaceutical products and can be excreted intact, such as after the active agent is released.

The active agents described herein can include any one or more of the following: therapeutics, diagnostic agents, and agents for altering the local properties of the gastrointestinal system. For example, therapeutics can include peptides, proteins, antibodies, oligonucleotides, polysaccharides, and/or small molecule organic drugs. In some embodiments, the active agent can include a formulation or agent composition which may be used for treatment of a disease. For example, the active agent can include a drug that can be delivered to the GI tract wall of a patient. The active agent can also be used for diagnostics in which the active agent can contain an imaging agent. In some embodiments, the active agent can be configured to provide a physical barrier, such as a coating, along a part of the GI tract. In some embodiments, the coating is used for therapeutic purposes such as sealing the surface or ablating the surface of the GI tract to achieve a metabolic effect, or for treating a disease of excess permeability of the GI tract such as celiac disease, or for sealing a wound. The delivered agent can also be used for altering the pH or buffer strength of the local environment in the GI tract, or may contain a material designed to alter the properties of the GI tract tissue surrounding the capsule delivery device.

In some embodiments, the capsule delivery device can be configured to deliver an active agent into the GI tract after exposure to a fluid or substance within a particular pH range (e.g., a pH typically found in the GI tract), and/or after a predefined time (e.g., a time to allow the device to pass from the oral cavity to the desired active agent delivery location, such as the intestines), and/or exposed to a pressure within a particular pressure range. For example, the capsule delivery device can be configured to dispense (e.g., spray) a formulation including an active agent using a propulsive force generated inside the capsule delivery device (e.g., by a spring or other propulsion mechanism). In some embodiments, activation of the active agent delivery may be done remotely using a remote signal wirelessly (e.g., triggering a release of a gas for use as the propulsive force). The active agent may be delivered onto the surface of the GI tract and into the wall of the GI tract at depths which depend on the force used to dispense the active agent. The active agent may be delivered as a spray onto the surface of the GI tract or as a stream to penetrate the surface of the GI tract, which is controlled by the type of nozzle or delivery port configuration.

The capsule delivery device can allow for precise and effective delivery of an active agent in an amount that is effective for treating or diagnosing a subject (e.g., human, animal). In addition, delivery of therapeutic agents into and onto the wall of the GI tract is useful for putting a therapeutic agent into the highly vascularized tissue of the gut where it will be rapidly absorbed into the blood stream. This results in high bioavailability for poorly absorbed active agents, otherwise not achievable by standard formulation approaches. Various embodiments are described in greater detail herein.

Figure 1A:
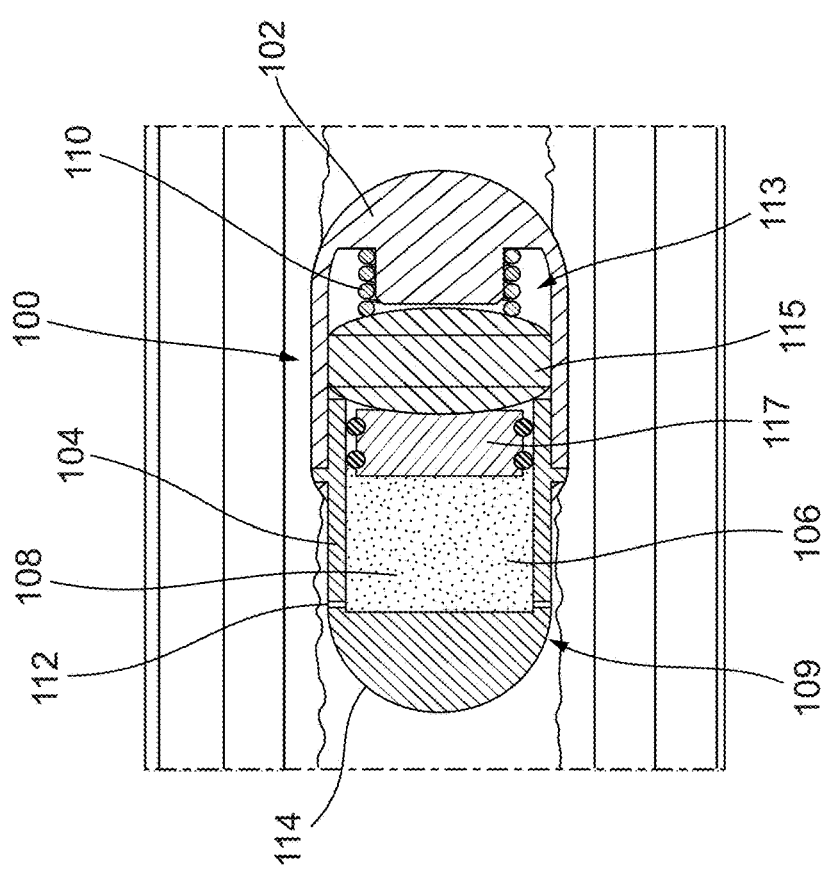
FIG. 1A illustrates an embodiment of a capsule delivery device containing an active agent, in accordance with implementations described herein.
Figure 1C:
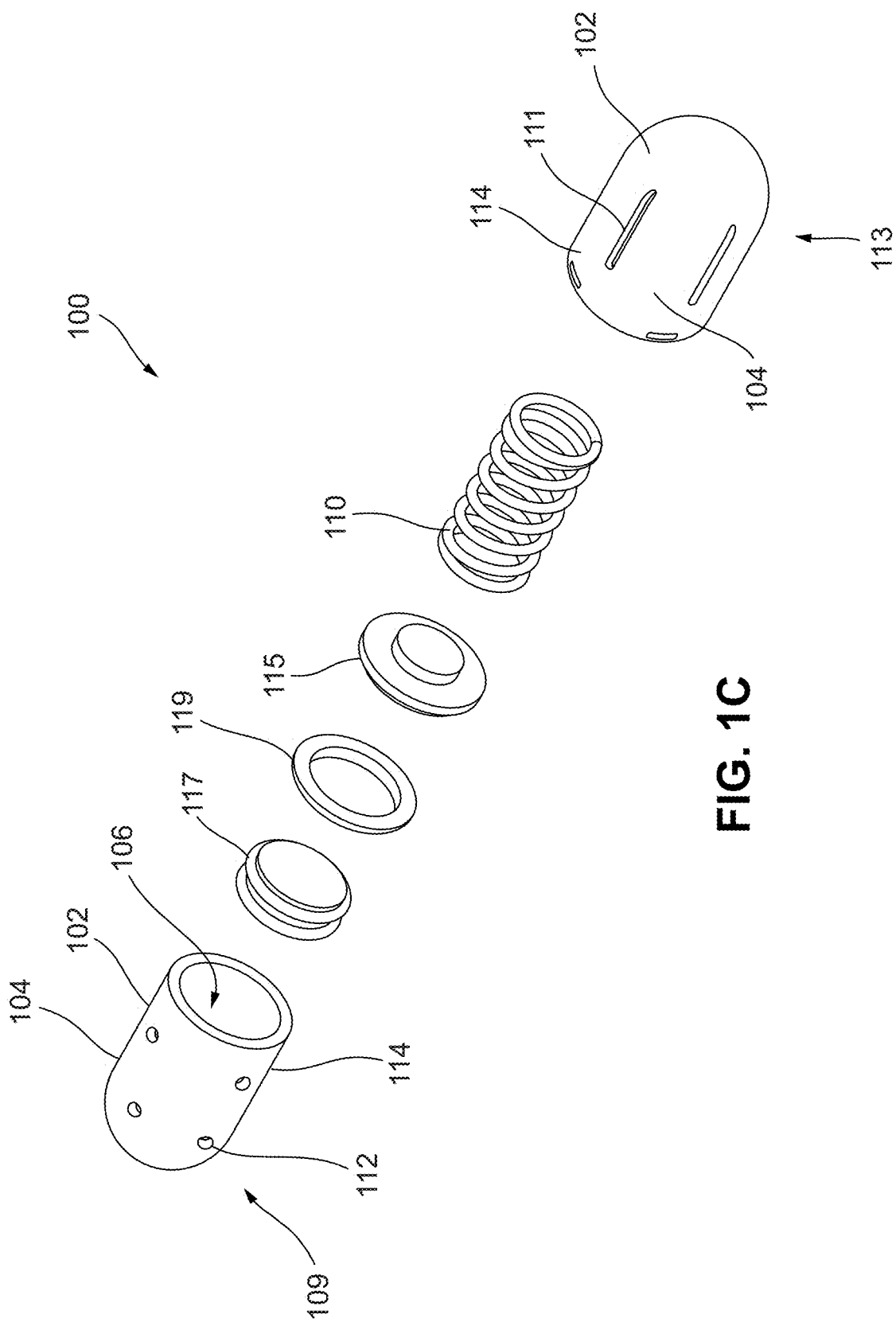
FIG. 1C illustrates an exploded view of an embodiment of a capsule delivery device.

FIGS. 1A-1C illustrate an embodiment of a capsule delivery device 100 including a capsule body 102 defined by a capsule wall 104 surrounding an inner body portion. As shown in FIG. 1A, the capsule body can be cylindrical in shape with opposing rounded ends. The capsule body can be made out of a single part or can include two or more parts that can be secured together, such as for ease of manufacturing. The capsule delivery device 100 further includes a reservoir 106 configured to contain one or more active agents 108, such as any of the active agents described herein and/or within the scope of this disclosure. The capsule delivery device 100 can also include an actuation feature 110 that is configured to provide a propulsive force that causes the active agent 108 to be delivered through a delivery port 112 positioned along the capsule body 102 to a part of the GI tract, such as any part of the GI tract discussed herein and/or within the scope of this disclosure. Additionally, the capsule delivery device 100 can include one or more delivery ports 112 positioned in one or more of a variety of configurations without departing from the scope of this disclosure.

In some embodiments, the capsule delivery device 100 can include a coating along an outer wall surface 114 of the capsule body, including over the delivery port 112. The coating can be configured to prevent fluid passage along the delivery port 112 when the coating is exposed to a first range of pH substances (e.g., fluids, air, etc.) and allow fluid passage along the delivery port 112 when the coating is exposed to a second range of pH substances (e.g., GI tract fluids). For example, fluids along the GI tract can include a pH that degrades the coating along the capsule delivery device outer wall surface 114 thereby allowing the active agent to be dispensed through the delivery port 112.

As shown in FIGS. 1A-1C, the capsule delivery device 100 includes an actuation control feature 115 that controls the ability of the actuation feature 110 to actuate. As such, the actuation control feature 115 also assists with controlling when the active agent is dispensed from the capsule delivery device 100. For example, the actuation control feature 115 can be positioned such that it retains the actuation feature in a first, non-activated position. Additionally, when the actuation control feature 115 deforms or dissolves, such change in the actuation control feature 115 can allow the actuation feature to transition from the first, non-activated position into the second, activated position. Such transition can allow the actuation feature 115 to provide the force necessary to deliver the active agent through the delivery port. In some implementations, a retaining ring or positioning feature 119, as shown in FIG. 1C, can assist with retaining a position of the actuation control feature within the capsule body 102.

For example, as shown in FIG. 1A, the actuation control feature 115 can include a tablet that can be dissolved as a result of contact with fluid, including GI tract fluid. For example, as shown in FIG. 1C, the capsule body can include one or more intake ports 111 that allow fluid to pass into an intake end 111 of the capsule delivery device. In the non-dissolved or solid form, the actuation control feature 115 can be positioned such that the actuation control feature 115 forces the actuation feature 110 to maintain the first, non-activated position (e.g., a compressed spring position). When the actuation control feature 115 becomes at least partially dissolved, the actuation feature 110 may no longer be retained in the first, non-activated position and, instead, is allowed to form the second, activated position, as shown in FIG. 1B. As the actuation control feature transitions into the second, activated position, the actuation feature 110 can act against a plunger 117 thereby advancing the plunger towards and into the reservoir 106 and delivery end 109 (e.g., including the delivery port 112) of the capsule body 102. Such advancement of the plunger 117 into the reservoir can force the active agent to be delivered through the delivery port 112, as shown in FIG. 1B. Other configurations and variations of actuation and active agent delivery are described herein and are within the scope of this disclosure.

In some embodiments, the intake port 111 can include semi-permeable features (e.g., liquid, water, gas, etc., designed to be selectively permeable) so that fluid from the GI tract is let into the inside the capsule body 102, such as for activating the actuation feature 110. In some implementations, the actuation control feature 115 can contain a medicinal drug (or not contain a medicinal drug), a coating agent, an imaging agent, or any material designed to change the local environment or GI tract tissue.

In some embodiments, the capsule delivery device 100 can include a coating along the outer wall surface 114 to facilitate traversal of the capsule delivery device 100 through the GI tract of a subject. For example, the outer coating can be enteric and/or include other pH sensitive, pressure sensitive, and/or a water soluble polymer coating. The coating may be used to seal holes (e.g., intake port 111, delivery port 112) of the capsule delivery device 100 to protect the contents, or to delay release, or to trigger release of the contents (e.g., active agents). The coating may also be a muco-adhesive polymer or other material that is used to retain the capsule against the surface of the GI tract to enhance the contact time and the delivery efficiency from the capsule device 100.

In some embodiments, the capsule delivery device 100 can include a plurality of delivery ports 112 positioned radially around the cylinder-shaped capsule body 102 so that the active agent may be sprayed out of all sides of the capsule at once. In another example, the delivery ports 112 may be arranged linearly along the length of the capsule body 102. In another embodiment, an array of delivery ports 112 may be wrapped all the way around the cylinder body. In addition, a spray sheet may be achieved by modifying the opening of the delivery port 112. In some embodiments, one or more delivery ports 112 or intake ports 111 may be used to spray a fluid that causes propulsive energy such that the capsule body is forced in a certain direction. For example, the capsule body 102 may be forced by the opposing spray against one side of the GI tract for intimate contact with the GI wall.

Spraying more than one formulation (e.g., active agent) can require that more than one delivery port 112 is connected to more than one reservoir or to a co-formulation of more than one drug, or more than one drug and any other additives such as stabilizing excipients and/or active permeabilizing excipients. The different sprays may include a multitude of drug formulations, drug formulation(s) plus a spray designed to move the capsule body 102 in a given direction, a non-drug containing formulation designed to alter the local contents of the GI tract, or a combination of any of the above. The spray may be set up using a pulse signal or staggered release of formulation out of the capsule body 102.

Each delivery port 112 can be of a single diameter or tapered. In some implementations, a diameter of a delivery port 112 can be 20 to 200 µm, and preferably about 100 µm. In some implementations, the length of the delivery port 112 may be proportional to the diameter, for a desired flow of the formulation. Preferably, the length of the delivery port 112 is equal to the diameter of the delivery port 112, with a pitch of about 5 to 50 µm, such as 10 µm.

In some embodiments, a proximal end of the capsule device can contain a cover or cap for the delivery port 112 that contains a polymer which is configured to expand when exposed to the fluid in the GI tract. As the polymer expands it forces the proximal end of the capsule device to be removed from the rest of the capsule device, to thereby uncover the delivery port 112 and allow delivery of active agent. In this way, the delivery ports 112 can be protected until they are placed into the GI tract. Alternatively, the delivery port 112 are along the capsule wall 104 of the capsule body 102 and are plugged using enteric coated pH sensitive polymer that prevent fluid flow through the delivery port 112 until exposed to a pH of the GI tract.

The proximal or intake end 113 can include a semipermeable membrane which allows GI fluid to contact the polymer. The semi-permeable membrane may be designed to allow water, gas, or other stomach contents to pass through. For example, the polymer can be caused to dissolve by interacting with the water in the GI tract fluid. In another example, the polymer only dissolves when the fluid of the GI tract reaches a certain pH.

In some embodiments, the actuation control feature 115 may be a standard excipient-based tablet containing no drug, may be enteric coated, and/or may contain a drug, a diagnostic, and/or an agent that alters the local environment of the GI tract upon release. The intake ports 111 can be either kept open or can be filled with enteric polymer such that the intake ports 111 are opened at a desired pH, thereby exposing the actuation control feature 115 to the GI fluid. In some embodiments, the actuation control feature 115 disintegrates, and simultaneously releases a first reacting agent in the capsule body 102 containing a second reacting agent, while also allowing the actuation feature 110 to be activated (e.g., spring is released and expands, or gas is created as propulsive force), thus delivering the active agent from the reservoir 106 through the delivery ports 112.

Various different kinds of polymers or materials may be used to trigger dissolution of the actuation control feature 115, as well as for coatings of the delivery ports 112. For example, suitable pH sensitive enteric polymers (e.g., Eudragit®, and other polymers with timed release) may be used, such as depending on the thickness of the coating used, and/or multiple layers of polymers may be used. Some polymers may be triggered to dissolve at pH 5.5, 6.0, or 7.0 depending on the polymer used. Other materials known in the art are sensitive to degradation in the colon may also be used for the actuation control feature 115 coating material to trigger its release, as well as the plugs for the delivery ports 112. For example, pectin and ethyl cellulose are carbohydrates which can be dissolved only in the colon where the amylase, pectinylase, and other enzymes have higher concentration and are more active. In addition, other insoluble coating and plug materials may be used to achieve timed release, or used in combination with the pH and enzyme sensitive polymers to provide additional control for the dissolution of the actuation control feature 115 and the clearance of the delivery ports 112.

The physical properties of the spray can depend on the length, diameter, and shape of the delivery ports 112, as well as the physical properties of the formulation such as viscosity, and the force applied to the formulation. Important properties of the spray are the diameter of the spray, the velocity of the spray, the viscosity of the formulation, and the composition of the formulation. Varying all of these in one direction or the other creates wider or narrower sprays, higher or lower velocity sprays, and with higher or lower velocities.

Different spray properties can be used to treat the inner wall of the gut differently. For example, the inner surface of the gut where villus are coated with a mucus layer to protect the lining of the gut may be a primary barrier for getting drugs absorbed into the blood stream. A spray of active agent onto the surface and in between the villi can be useful to enhance oral bioavailability of active agents without penetrating the wall of the gut. In addition, agents may be sprayed onto and between the villi to improve or restore the tissue which has been damaged in certain disease states of the GI tract, such as Chron's, colitis, inflammatory bowel disease, Celiac disease, and/or necrotizing enterocolitis. Additionally, there are mucosal glands and lymph nodes located at the base of the villi which may be treated with a surface sprayed active agent to up or down regulate the immune system, such as in the case of a vaccine.

The delivery port 112 can be oriented perpendicular to the transit down the GI tract so that fluid flow is directly into the wall of the intestine, however the delivery port 112 can be oriented at any particular angle along the capsule body 102 for directing fluid to the intestinal wall. A diameter and/or length of the delivery port 112 can be designed based on fluid flow and forces used in injector systems through small gauge needles, as well as the forces and properties associated with needle-free injectors useful for skin delivery.

In some embodiments, the actuation control feature 115 can be configured to be fast dissolving and rapidly expanding. In some embodiments, the actuation control feature 115 can include an active therapeutic agent, a diagnostic agent, and/or a material designed to alter the pH or other property of the local GI tract (e.g., to soak up the local fluid, or thin the local fluid such as with a surfactant, etc.).

The capsule body 102 can be formed of any size, and can also be formed of any material. For example, any component of the capsule delivery device 100 can be formed of a dissolvable substance such as hard gelatin. The capsule delivery device 100 can also be sized appropriately for travel along a GI tract and/or for oral delivery, i.e., enlarged or miniaturized for use with animals. The capsule body can include more than one part (e.g., two parts coupled together) and any part can be injection molded with one or more of a variety of materials (e.g., cyclic olefin polymer or other pharmaceutically acceptable materials).

In some implementations, the delivery port 112 diameter can range between approximately 20 microns to approximately 200 microns, such as between 50 microns to 150 microns. In some implementations, the capsule delivery device 100 can be configured to generate approximately 5 pounds per square inch (PSI) to approximately 20 PSI of pressure for active agent delivery, such as in order to penetrate tissue with the active agent. Spray through one or more of the delivery ports 112 can reach a velocity of greater than 10 meters/second, and more preferably greater than 25 meters/second, which can penetrate small intestine tissue.

Velocity of the spray can be related to delivery port 112 diameter, number of delivery ports 112, viscosity of fluid, and force applied by the actuation feature 110. The depth that the spray reaches into the gastrointestinal tissue may depend on the application and can be directly proportional to the velocity of the spray. In some applications, greater than 25 meters/second will be required to reach a depth of penetration into GI tissue of 1.5 to 2 mm, which may reach the submucosa. Accordingly, a delivery port 112 diameter can be approximately 20 µm to approximately 200 µm, such as approximately 100 µm. In some applications, the target tissue may be the lymph nodes at the base of the villi and may not require tissue penetration and, instead, mucous layer penetration thereby requiring a lower velocity of fluid or different kinds of fluid to be used in the formulation with different viscosities. In some applications, the top of the villi may be targeted with a fluid stream or spray, and may require even lower velocity to achieve surface coating.

Figure 2B:
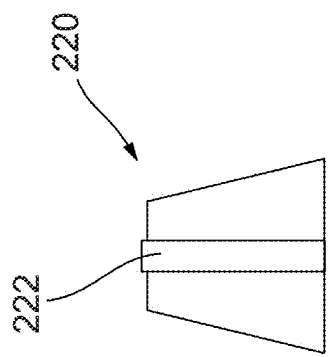
FIG. 2B illustrates an embodiment of a nozzle that can be releasably coupled to the delivery port of the capsule delivery device of FIG. 2A.

Formulations (e.g., active agents) may have a variety of medicinal drugs in them, vehicles that do not contain drugs, and vehicles with agents that are designed to alter the properties of the surrounding environment in the GI tract, as well as formulations containing imaging agents, and formulations designed to soak up the fluid in the surrounding environment, as well as formulations designed to treat the tissue of the GI tract. Formulations may be homogeneous aqueous or non-aqueous solutions, suspensions in aqueous or non-aqueous vehicles, or dry powders that are reconstituted by a fluid prior to spraying, or dry powders that are sprayed into the GI tract. Such options may require different delivery port 112 configurations (e.g., including various nozzle configuration, as discussed below with reference to FIGS. 2A and 2B), different propulsive forces, and/or different capsule body configurations. Formulations may contain drugs such as peptides, proteins, antibodies, enzymes, oligonucleotides, polysaccharides, organic compounds, vaccines. Drugs may be used to treat topical diseases of the GI tract, diseases of the surface tissue in the GI tract, or disease that are systemic wherein the drug must permeate through the GI tract into the blood.

Alternatively, formulations may contain agents designed to alter the properties of the environment surrounding the capsule, such as pH changes, viscosity changes, tissue permeability changes, etc., such as: agents to change pH include naturally occurring acids and bases; agents to change the viscosity by reducing it include surfactants, lipids, fatty acids, and agents to change the viscosity by increasing it include thickening agents such as sugars, carbohydrates, polymers, etc.; and naturally occurring materials. Further, a formulation can include one or more agents to increase the permeability of the GI tissues including known permeation enhancing agents such as oils, medium chain triglycerides, lauryl carnitine, caprylic acid, and surfactants such as sodium lauryl sulfate, and/or lipids. Formulation may contain agents that are designed to enhance permeability of the GI tract by including agents that reduce the efflux from the GI tissue such as polyethylene glycol, and other excipients known to reduce efflux. Alternatively, formulation may contain agents that are known to reduce the permeability of the GI tract tissues, such as vasoconstrictors, and other agents designed to make tight junctions tighter, and improve the integrity of the GI tract tissue. Certain diseases exhibit either elevated permeability (e.g. celiac disease) or reduced permeability of the GI tissue. Formulations may contain excipients that are designed to reduce the viscosity of the mucous layer over the villi, or to dissolve the mucous layer altogether.

Formulations may contain imaging agents that are designed to image various locations of the GI tract and tissue of the GI tract, such as positive contrast materials for radiography or MRI. Formulations may also contain spasmolytics such as glucagon or butylscopolamine in order to reduce motion artifacts during imaging of the GI tract. Formulations may contain agents designed to ablate the surface of the GI tract to promote growth of new tissue, as exemplified in the ablation device being promoted by fractyl labs, designed to alter the course of metabolic disease. These agents may be acidic or basic, lipid or surfactant in nature, and designed to remove the surface layer of the tissue of the GI tract.

Formulations may contain biodegradable polymers or biocompatible glue designed to cover the surface of the GI tract to repair wounds such as ulcers or lesions, or to cover certain portions of the GI tract, such as was the purpose for the GI Dynamics plastic sleeve, intended to alter the course of metabolic disease. The polymer or glue formulation may contain agents that cause or inhibit inflammation or other biologic functions that are designed to remove the upper surface of the GI tissue as they slough off the tissue.

Non-viscous formulations are low viscosity and comparable to water with viscosity of 1 centipoise (cps) and up to about 50 cps, which is comparable to corn oil. The force required by the actuation feature to deliver such formulations may be approximately 10 N, or less than 50 N.

Viscous formulations may have a viscosity above 50 cps (such as corn oil, for example) and as high as 10000 cps (such as molasses, for example). Such compositions can be highly concentrated drugs such as antibodies, proteins, peptides, small molecules, etc. in aqueous vehicles, or may also be formulations using non-aqueous vehicles for the purposes of increasing stability of the composition. The force required by the actuation feature to deliver such formulations may be approximately 10 N and may be as high as 50 N or 100 N. Alternatively, the diameter of the delivery port 112 may be widened to accommodate the higher viscosity solutions and reduce the force requirement.

In some embodiment, the delivery port 112 may be configured to allow an active agent including a suspension of a well dispersed particle with a defined particle size distribution. For example, the size of such particles may be as high as 200 microns and as small as 1 nm to 10 nm in size, and may be preferably less than 100 microns and greater than 50 nm, and more preferably less than 50 microns and greater than 100 nm is diameter.

Dry powder formulation compositions may be designed to be reconstituted or suspended during the delivery process in the capsule delivery device. For example, particles to be reconstituted prior to emission from the delivery port 112 may need to be able to solubilize in the active agent instantaneously and may likely be fluffy lyophilized powders being reconstituted in an aqueous vehicle, but, could alternatively be a powder that may be instantaneously solubilized in a non-aqueous vehicle suitable for pharmaceutical use. Such particles can be amorphous so that they dissolve quickly, but may be crystalline if they dissolve quickly in a suitable vehicle. Particle diameter can be less than 1 mm in size to ensure rapid dissolution in the active agent, and may be less than 100 micron in diameter. The device configuration for the powders to be reconstituted contains an extra reservoir which allows the vehicle to be stored separately from the dry powder, and a mechanism for allowing mixing of the dry powder prior to being emitted from the nozzle.

Formulation compositions can be prepared as dry powder designed to be emitted from the device as a dry powder. Such formulations can include small and large particles, or mixtures of small and large particles, as well as particles configured into a specific form such as a spear designed to pierce the GI tissue, amorphous and crystalline powders obtained directly from a lyophilizer or a precipitation or crystallization, powders prepared by spray-drying, jet-milling, or other techniques, powders mixed with other powders such as those used in traditional dry powder inhalers, powders designed in the nanometer to micron size range (0.1 micron to 5 microns) such as those designed for inhalation powders, particles in the low to mid micron size range (10 to 30 microns) such as those designed for nasal spray powders, powders in the mid to large micron size range (30 microns to 500 microns) such as those designed for use in conventional oral tablet formulations (methyl cellulose and the like).

Formulations intended to be delivered as a reconstituted suspension can be easily dispersible in the formulation so they can be mixed quickly and do not plug the channels of the device and nozzle prior to homogeneous mixing. The particle size of such materials can be comparable to those described above for the suspension formulations. Excipients may be used in the formulation or in the particle composition to increase dispersibility of the particle in the formulation.

Formulations may also be long-acting formulations as suspensions or solutions. For example, since the capsule delivery device 100 can deliver solutions or suspensions, the potential for including long-acting injectables into the capsule delivery device 100 is feasible along with the active agent long half-life molecules. Various Jong-acting formulation, including suspensions, can be used with the capsule delivery device embodiments described herein. For example, gel-forming polymer that includes a 1 month, 3 month, 4 month, and/or 6 month exposure profile can be included in the capsule delivery device. In another example, medications like those used in schizophrenia as long-acting nano- and micro-suspensions for 1 to 3 month injection frequency can be delivered from the capsule into the wall of the GI where they can form a slowly dissolving drug depot or reservoir. In this way, the capsule can be used for ultra-long oral delivery products with administration frequencies of weekly or monthly or longer.

In some embodiments, the plunger 117 can include one or more O-rings that can be configured to provide a predetermined amount of resistance against the spring, for measured expulsion and delivery of the formulation. In some implementations, the capsule device can include a tablet reinforcement bushing 119 or the like, which can aid in securing the tablet in position when the capsule body is being filled, or is filled, with the formulation.

One or more features may be added to the capsule body 102 to enhance adhesion or attractiveness of the capsule surface to the wall of the gut. Surface coatings may be used for muco-adhesion or mucous penetration. The capsule can be coated with a mucous penetrating polymer like those defined in the literature, such as polyethylene glycol, and others. The capsule could also be coated with or manufactured from muco-adhesive materials, such as polymers, chitosan, etc.

Physical changes in the outer surface of the capsule 102 may be used for making it attract to the lining of the GI tract. This can be done with striations on the capsule outer surface like a corrugated material to increase the surface area making it natural to adhere to the wall of the GI tract, or by making the surface rough like sand paper. The surfaces may have a plurality of grooves that may be configured in a screw-like configuration along the capsule length, or straight up and down or perpendicular to the capsule length. They may be dimpled and convex or dimpled and concave. They may be sponge-like with imperfect and non-homogeneous surfaces. They may be radially oriented around the cylindrical surface. Such surface modifications can be covered by enteric coated polymer so the capsule is smooth for easy swallowing. Once in the upper GI or region of the GI tract where the enteric coat dissolves, the capsule would present with the modified surface designed to adhere to the wall of the GI tract.

The outer surface of the capsule may be oriented so that it spins toward the wall of the GI tract, such as when propelled. For example, this can be accomplished by creating a spiral-like surface on the capsule device that will allow it to bore into one or more surface layers of the GI tract (e.g., mucous layers) and embed therein, such as without penetrating a surface layer. The outer surface of the capsule device can be configured to spin the capsule and move it toward the lining of the GI tract, such as when the capsule device is propelled. The surface modifications can also be designed to orient the capsule nozzles or delivery ports closer to the GI tract lining compared to the other end of the capsule device, thereby increasing the contact of the nozzles or delivery ports to the wall of the GI tract.

In some embodiments, the actuation control feature 115 may contain materials that react to produce a propulsive force as the actuation control feature 115 (e.g., tablet) dissolves, thereby moving the capsule body 102 toward the wall of the GI tract. The actuation control feature 115 may contain excipients only, materials to modify the local environment, but, may also contain excipients that are used to propel the capsule body 102 toward the wall of the GI tract. The propulsion may come from a bicarbonate or other material that is designed to be released and react with the local environment to create a small explosion or expulsion of gas. This may be bicarbonate, sodium azide (used in airbags in cars), or other water and acid or base reactive material that releases a gas upon exposure to the local GI tract. These excipients may also be standard immediate release excipients that are designed to cause the tablet to disintegrate quickly.

In some embodiments, the intake ports 111 on the intake end 113 of the capsule body 102 may be oriented and configured to produce a jet propulsion that pushes the capsule body toward the wall of the gut when the actuation control feature 115 dissolves and creates a propulsion force. In the case where the actuation control feature 115 rapidly dissolves and produces a propulsive gas, the gas can be expelled through one or more intake ports 111 or vent ports in the sides of the capsule body. Such ports can be shaped and positioned so that the capsule body can be pushed in at least one direction when the gas is expelled. For example, ports for releasing propulsion forces (e.g., intake ports 111) may be only on one side of the capsule body 102 (e.g., intake end 113) opposite to where the delivery ports 112 are located (e.g., on the delivery end 109) such that propulsion moves the capsule toward the GI wall so that the delivery port distance to the GI wall is minimized. In some embodiments, the intake ports 111 can be oriented to spin the capsule body 102 when propulsion forces or gases are released through the intake ports 111. For example, the intake ports 111 can either be oriented perpendicular to the wall of the capsule body 102, in which case the capsule body 102 can, for example, move laterally across the gut perpendicularly toward the wall of the GI tract. Alternatively, the spinning action can move the capsule device 100 longitudinally along the length of the gut so that the capsule device 100 spins closer to the wall of the GI tract. The spinning action can be used in concert with the surface modifications to move the capsule device 100 closer to the wall of the GI so the delivery ports 112 are oriented with minimum distance from the wall of the GI tract.

Figure 2A:
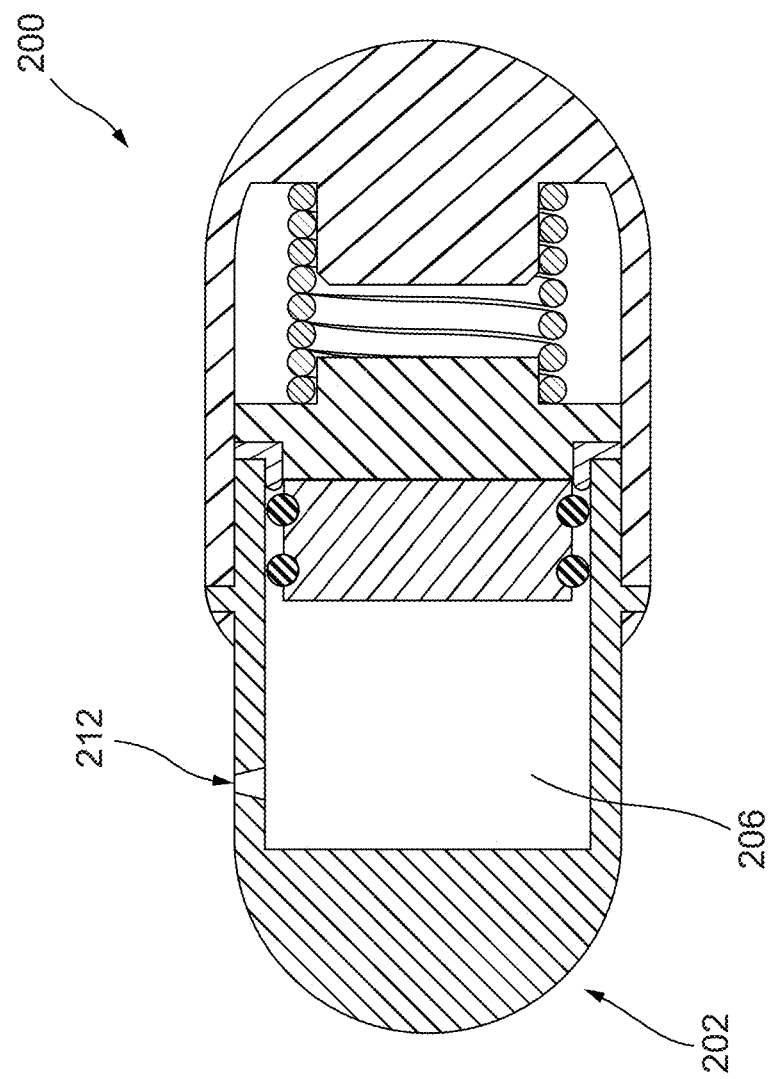
FIG. 2A illustrates another embodiment of a capsule delivery device showing a delivery port.

FIG. 2A illustrates another embodiment of the capsule delivery device 200 including a delivery port 212 in communication with the reservoir 206. The delivery port 212 can be configured to receive a nozzle, such as the nozzle 220 illustrated in FIG. 2B. In some embodiments, the nozzle 220 can be releasably coupled to the delivery port 211. The nozzle 220 can include a fluid passageway 222 that can control and/or effect the type of spray or stream of active agent from the capsule body 202. For example, in some embodiments, the nozzle 220 can be configured to generate a spray of the active agent. In some embodiments, the nozzle 220 can be configured to break up the active agent in separated drops and direct the liquid drops onto or into the adjacent tissue. The nozzle 220 can be designed with varying lengths and diameters to generate fluid sprays or streams of varying velocity and width. For example, a wide stream with a low velocity may be used to deliver the active agent onto the surface of the GI tract. A medium spray with a medium velocity, for example, may be used to penetrate a thick and viscous mucin layer and to deposit the active agent onto the surface of the GI tract. A high velocity narrow spray, for example, may be used to penetrate the GI tract tissue at varying depths, such as to achieve enhanced bioavailability on the surface of the gut wall or into the systemic circulation. All of the configurations of the nozzle described herein are applicable to this replaceable nozzle system.

The capsule delivery device 200 including the delivery port 211 configured to releasably couple various nozzles 220 can allow one capsule body to be manufactured and multiple different configurations and types of nozzles 220 to be used, such as for achieving various spray or stream delivery configurations of the active agent. For example, five delivery port 211 can be radially oriented around the capsule body 202. Two of the delivery ports 211 can be plugged (e.g., with a plug made of plastic or other materials) and three of the delivery ports 211 can each be coupled with a nozzle 220. Each of the nozzles can be the same or different. The nozzle may be coupled to the delivery port 211 in a variety of ways (e.g., via friction fit, welded, threaded, etc.).

In another configuration, the capsule delivery device can be configured to be manufactured as a complete empty system and allowed to be filled, such as just prior to use.

Figure 3:
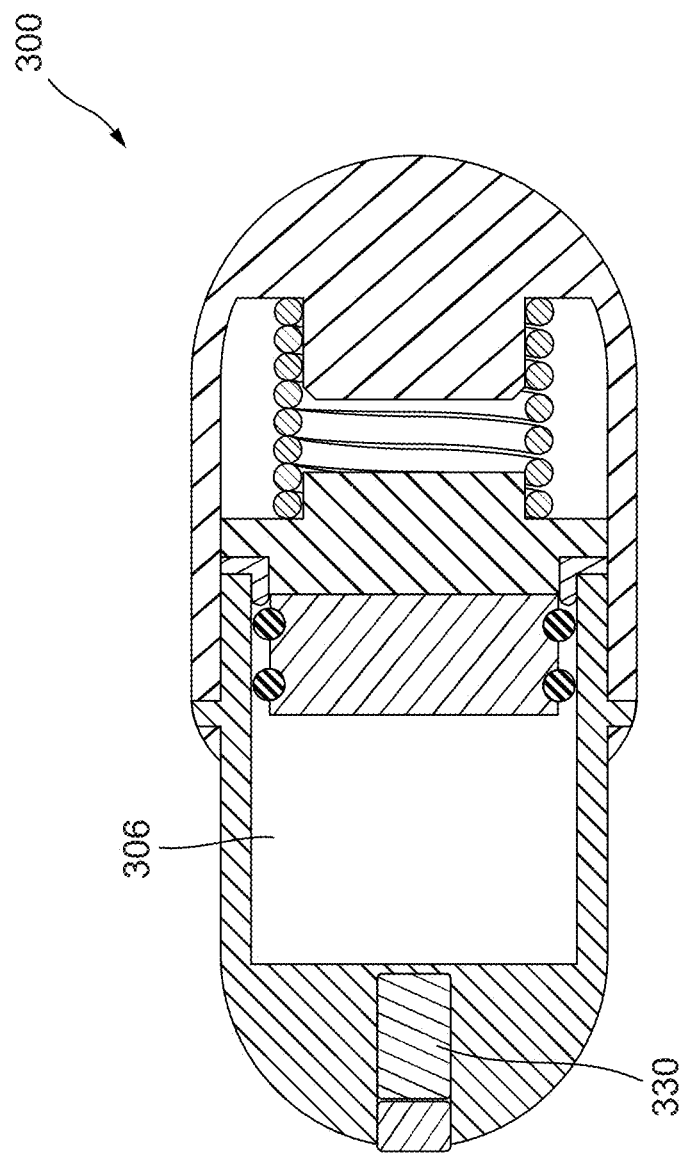
FIG. 3 illustrates another embodiment of a capsule delivery device showing a fill port including a septum.

FIG. 3 illustrates another embodiment of a capsule delivery device 300 including a septum 330 for allowing filling of the reservoir 306 with an active agent. To achieve this, the capsule can be provided in a configuration that is complete and ready to be used once filled with an active agent, as shown in FIG. 3. The reservoir can then be filled, such as by inserting a needle of a syringe through the septum. For example, filling of the reservoir can be completed with a disposable syringe or precision glass syringe with metal barrel for improved accuracy of delivering small volumes.

In some embodiments, the internal volume of the reservoir (e.g., reservoir 106, 206, 306) of the capsule delivery device can include approximately 0.5 mL to approximately 1.0 mL, and thus contain approximately 0.5 mL to approximately 1.0 mL of substance volume (e.g., containing formulation and/or active agent). In some embodiments, the reservoir can include a volume of approximately 0.05 mL to approximately 0.5 mL, such as approximately 0.1 mL to approximately 0.4 mL.

In some embodiments, depending on the active agent concentration, the reservoir volume can contain active agent quantities directly proportional to volume. For example, higher volumes (e.g., 1 mL) may be capable of delivering between 100 mg and 200 mg for active concentrations of 100 mg/ml and 200 mg/ml. Higher concentration of active agent can allow larger amounts to be delivered. A typical minimum quantity for delivery of active agent can be between approximately 5 mg to 10 mg and up to 30 mg to 50 mg and can depend on the volume delivered as well as the concentration of the active agent.

Figure 4:
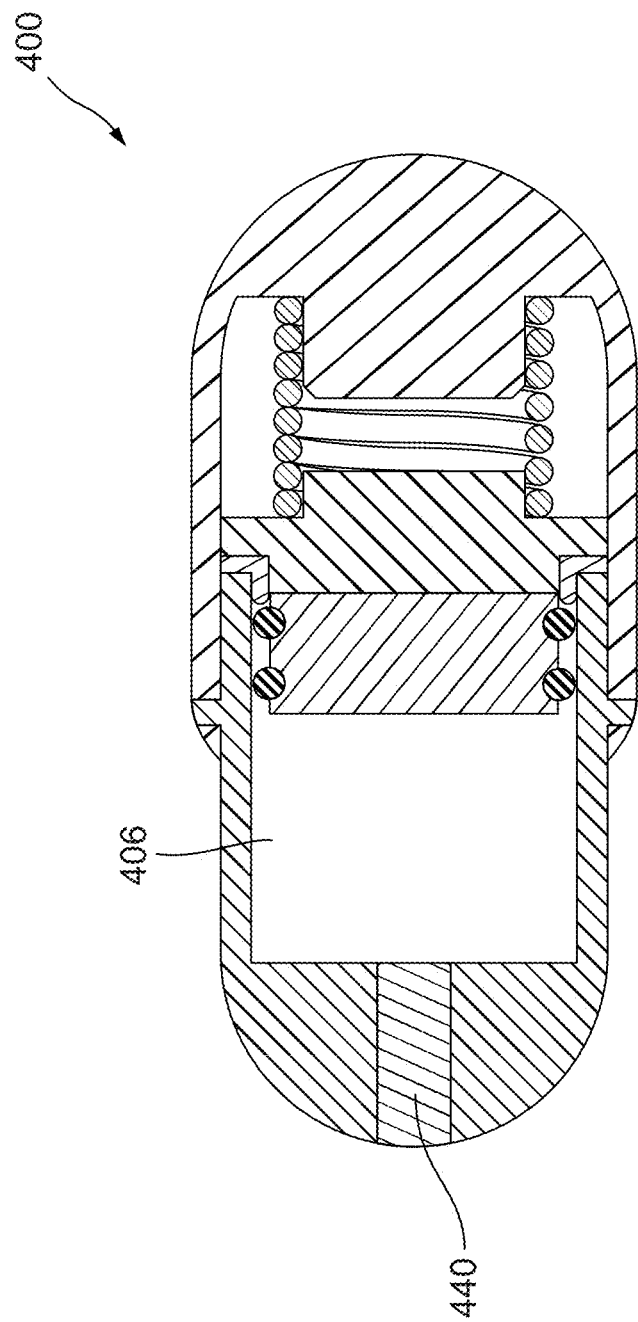
FIG. 4 illustrates another embodiment of a capsule delivery device showing a threaded fill port.

FIG. 4 illustrates another embodiment of a capsule delivery device 400 including a filling port 440, such as on an end of the capsule body, which can allow a simple filling process of the reservoir 406, as well as use with standard filling lines for liquid or suspension products. For example, the fill port 440 may be formed out of plastic or other suitable material compatible with the active agents in the reservoir 406. The filling port 440 may have screw threads that allow a fill plug to threadably couple and seal to the fill port 440. For example, the fill plug may have O-rings or other flanges built in to help it stay in place and form a seal.

In some embodiments, the delivery end 109 of the capsule delivery device can be releasably coupled to the intake end 113. Additionally, the delivery end can include a cone or rounded cap shape, and can also include a delivery port 112 and/or nozzle. For example, the delivery end 109 can threadably mate (e.g., screwing mechanism) or can be welded to the intake end 113. Such coupling can form and seal the reservoir 106. In some embodiments, the delivery ports can be drilled or created from microfluidic technology, MEMs, or other micro-machining techniques.

Figure 5:
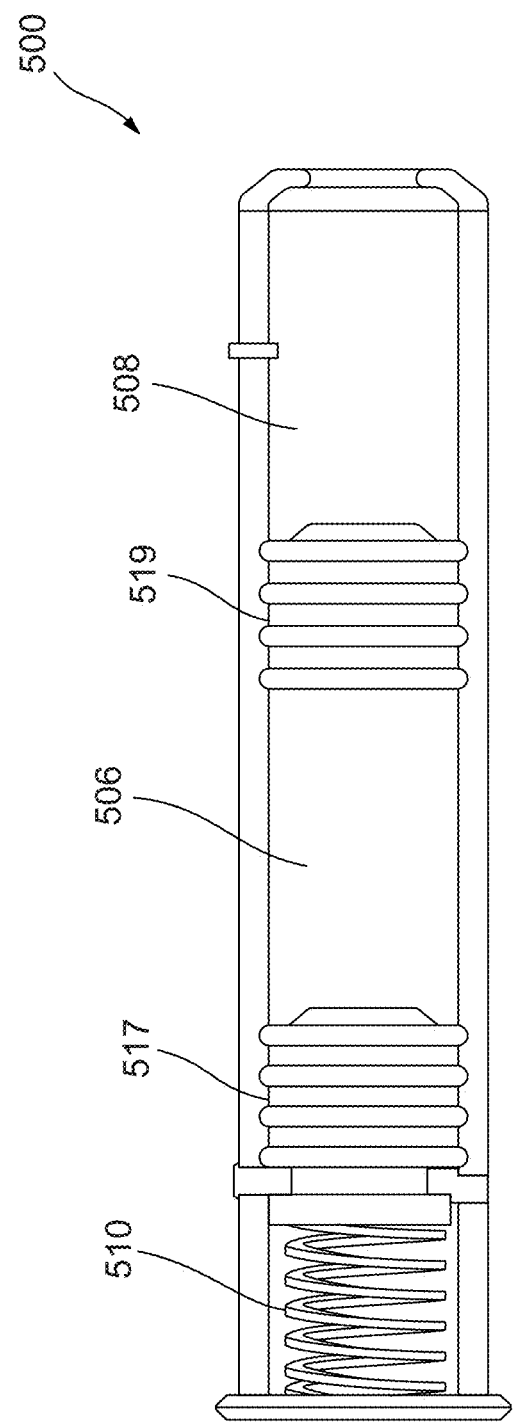
FIG. 5 illustrates another embodiment of a capsule delivery device including two plungers and two reservoirs.

FIG. 5 illustrates another embodiment of the capsule delivery device 500 including at least one actuation feature 510 (e.g., a spring) and more than one reservoir and plunger. For example, the actuation feature 510 can cause a first plunger 517 to advance and cause a first active agent contained in a first reservoir 506 to be dispensed. Additionally, actuation of the actuation feature 510 can cause the second plunder 519 to advance and cause a second active agent contained in a second reservoir 508 to be dispensed.

In some embodiments, the capsule delivery device 500 can include one or more plugs to hold the actuation feature 510 in place or in a biased state, prior to exerting the propulsion force to the first plunger 517. Materials that can be used to hold the actuation feature 510, such as spring, for example, in place until triggering can include an osmotic plug, water soluble plastic, pH sensitive polymer, or glue with similar properties, or a standard pharmaceutical tablet designed to rapidly degrade and disintegrate in the presence of GI fluid. Likewise, a trigger mechanism for the actuation feature 510 can include a water soluble or pH sensitive plastic, polymer, or glue, or the like.

Use of the capsule delivery device may not be confined to use as an oral swallowed capsule. For example, some embodiments of the capsule delivery device may be used as a rectal suppository designed to release drug based on triggers by the environment. Some embodiments of the capsule delivery device can be used as a vaginal insert for delivery of agents to the inside of the vagina. Some embodiments of the capsule delivery device can be miniaturized for use as an ocular insert under the lid of the eye or as a device designed to spray material into the oral cavity, such as to the buccal or sublingual space, for both topical treatment of the oral cavity with active agent, or for penetration of the oral cavity tissue for enhancing bioavailability into the blood of an active agent.

Although some embodiments have been described in detail above, other configurations are within the scope of this disclosure.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

The invention claimed is:

1. An oral delivery capsule device for delivering an active agent to a part of a gastrointestinal tract of a subject, comprising: a capsule body configured to travel along the gastrointestinal tract, the capsule body having a capsule wall defining an inner body portion; a reservoir positioned in the inner body portion and configured to contain the active agent for delivery to the part of the gastrointestinal tract of the subject; an actuator configured to provide a delivery force to the active agent thereby causing a dispensing of the active agent from the capsule body through a delivery port along the capsule wall; and an actuator control configured to prevent actuation of the actuator under a first condition and allow actuation of the actuator under a second condition, wherein the actuating of the actuator control creates a propulsion force through a vent extending through the capsule wall thereby propelling the capsule device toward a surface of the gastrointestinal tract.

2. The oral delivery capsule device of any of claim 1, further comprising a coating positioned over at least the delivery port and configured to prevent fluid passage through the delivery port when the coating is exposed to a first pH range and allow fluid passage through the delivery port when the coating is exposed to a second pH range.

3. The oral delivery capsule device of claim 1, wherein the actuator control includes an enteric coated tablet configured to dissolve when under the second condition, the second condition including exposure to a gastrointestinal fluid having a pH within a predefined pH range.

4. The oral delivery capsule device of claim 1, wherein the actuator control includes a polymer coated tablet configured to dissolve when under the second condition, the second condition including a passage of a pre-defined time.

5. The oral delivery capsule device of claim 1, wherein the actuator includes a biodegradable plastic that dissolves when under the second condition, the second condition including contact with gastrointestinal fluid.

6. The oral delivery capsule device of claim 1, wherein an outer surface of the capsule wall includes a coating including a muco-adhesive material that assists with mating of the capsule body to the part of the gastrointestinal tract.

7. The oral delivery capsule device of claim 1, wherein an outer surface of the capsule wall includes a surface feature that assists with mating the capsule body to the part of the gastrointestinal tract.

8. The oral delivery capsule device of claim 1, wherein the actuator control includes a propulsion formulation that creates the propulsion force after being placed in contact with a gastrointestinal fluid.

9. The oral delivery capsule device of claim 1, wherein the delivery port is configured to releasably couple a nozzle therein, the nozzle affecting a characteristic of fluid delivery from the delivery port.

10. The oral delivery capsule device of claim 1, wherein the delivery port further comprises a plurality of delivery ports positioned radially along a proximal end of the capsule body.

11. The oral delivery capsule device of claim 1, wherein the active agent includes one or more of a peptide, a protein, an antibody, an oligonucleotide, a polysaccharide, a small molecule organic drug, an inorganic drug, a therapeutic agent, a diagnostic agent, and a tissue coating agent.

12. The oral delivery capsule device of claim 1, wherein the capsule body is made out of a biocompatible and biodegradable material.

13. The oral delivery capsule device of claim 1, wherein the actuator includes a spring configured to transition between a first position and a second position thereby causing the dispensing of the active agent through the delivery port.

14. The oral delivery capsule device of claim 13, further comprising a plunger configured to advance towards the delivery port when the spring transitions between the first position and the second position.

15. The oral delivery capsule device of claim 1, wherein the second condition includes contact of a gastrointestinal fluid with the actuator control.

16. The oral delivery capsule device of claim 15, wherein the capsule wall of the capsule body includes an intake port configured to allow the gastrointestinal fluid to enter the inner body portion and contact the actuator control.

17. A method, comprising: receiving a gastrointestinal fluid through an intake port of a capsule wall of a capsule delivery device, the capsule delivery device comprising: a capsule body configured to travel along a gastrointestinal tract of a subject, the capsule body including the capsule wall defining an inner body portion; a reservoir positioned in the inner body portion and configured to contain an active agent for delivery to a part of the gastrointestinal tract of the subject; an actuator configured to provide a delivery force to the active agent thereby causing a dispensing of the active agent from the capsule body through a delivery port along the capsule wall; and an actuator control configured to prevent actuation of the actuator under a first condition and allow actuation of the actuator under a second condition; actuating, as a result of the gastrointestinal fluid contacting the actuator control, the actuator thereby providing the delivery force to the active agent and creating a propulsion force through a vent extending through the capsule wall thereby propelling the capsule device toward a surface of the gastrointestinal tract; and delivering the active agent through the delivery port of the capsule wall.

18. The method of claim 17, further comprising dissolving the actuator control as a result of the gastrointestinal fluid contacting the actuator control.

19. The method of claim 17, wherein actuating the actuator causes a plunger to be advanced along the reservoir thereby causing the delivering of the active agent.

20. The method of claim 17, further comprising a coating positioned over at least the delivery port and configured to prevent fluid passage through the delivery port when the coating is exposed to a first pH range and allow fluid passage through the delivery port when the coating is exposed to a second pH range.

21. The method of claim 17, wherein the second condition includes contact of the gastrointestinal fluid with the actuator control.

22. The method of claim 17, wherein the actuator control includes an enteric coated tablet configured to dissolve when under the second condition, and wherein the gastrointestinal fluid has the second condition including exposure to a fluid having a pH within a predefined pH range.

23. The method of claim 17, wherein the actuator control includes a polymer coated tablet configured to dissolve when under the second condition, the second condition including a passage of a pre-defined time.

24. The method of claim 17, wherein the actuator includes a biodegradable plastic that dissolves when under the second condition, the second condition including contact with the gastrointestinal fluid.

25. The method of claim 17, wherein an outer surface of the capsule wall includes a coating including a muco-adhesive material that assists with mating the capsule body to the part of the gastrointestinal tract.

26. The method of claim 17, wherein an outer surface of the capsule wall includes a surface feature that assists with mating the capsule body to the part of the gastrointestinal tract.

27. The method of claim 17, wherein the actuator control includes a propulsion formulation that creates the propulsion force after being placed in contact with the gastrointestinal fluid.

28. The method of claim 17, wherein the delivery port is configured to releasably couple a nozzle therein, the nozzle affecting a characteristic of fluid delivery from the delivery port.

29. The method of claim 17, wherein the delivery port further comprises a plurality of delivery ports positioned radially along a proximal end of the capsule body.

30. The method of claim 17, wherein the active agent includes one or more of a peptide, a protein, an antibody, an oligonucleotide, a polysaccharide, a small molecule organic drug, an inorganic drug, a therapeutic agent, a diagnostic agent, and a tissue coating agent.

31. The method of claim 17, wherein the capsule body is made out of a biocompatible material.

32. The method of claim 17, wherein the actuator includes a spring.

33. The method of claim 32, wherein the actuating includes allowing the spring to transition from a compressed configuration to an expanded configuration.

* * * * *